United States Patent [19]

Cole, Jr.

[11] Patent Number: 4,887,609

[45] Date of Patent: Dec. 19, 1989

[54] APPARATUS AND METHOD FOR FILTERING ELECTROCARDIOGRAPH SIGNALS

[75] Inventor: Malcolm P. Cole, Jr., Houston, Tex.

[73] Assignee: The Methodist Hospital System, Houston, Tex.

[21] Appl. No.: 49,668

[22] Filed: May 13, 1987

[51] Int. Cl.<sup>4</sup> .................................................. A61B 5/04
[52] U.S. Cl. ..................................... 128/696; 128/901; 128/653; 128/709
[58] Field of Search ................... 128/696, 303 B, 709, 128/901, 908, 653

[56] References Cited

U.S. PATENT DOCUMENTS

| | | |
|---|---|---|
| 3,316,897 | 5/1967 | Weidinger et al. . |
| 3,580,243 | 5/1971 | Johnson . |
| 3,903,874 | 9/1975 | Shakespeare . |
| 3,968,430 | 7/1976 | Maas ..................................... 128/901 |
| 4,000,461 | 12/1976 | Barber et al. . |
| 4,038,536 | 7/1977 | Feintuch ............................... 128/696 |
| 4,161,945 | 7/1979 | Grossman ............................ 128/696 |
| 4,192,318 | 3/1980 | Dam et al. . |
| 4,243,045 | 1/1981 | Maas ..................................... 128/696 |
| 4,245,649 | 1/1981 | Schmidt-Andersen ............. 128/696 |
| 4,408,615 | 10/1983 | Grossman ............................ 128/696 |
| 4,448,202 | 5/1984 | Wajszczuk et al. ................. 128/709 |
| 4,453,218 | 6/1984 | Sperinde et al. ..................... 128/696 |
| 4,478,224 | 10/1984 | Bailey ................................... 128/901 |
| 4,503,461 | 3/1985 | Nishimura . |
| 4,537,200 | 8/1985 | Widrow ............................... 128/696 |
| 4,614,195 | 9/1986 | Bottomley et al. . |
| 4,617,938 | 10/1986 | Shimoni et al. . |
| 4,751,931 | 6/1988 | Briller et al. ........................ 128/700 |

OTHER PUBLICATIONS

Lanzer, et al., *ECG-Synchronized Cardic MR Imaging: Method and Evaluation*, 155 Radiology 681 (1985).

*Primary Examiner*—Francis Jaworski
*Assistant Examiner*—George Manuel
*Attorney, Agent, or Firm*—Vinson & Elkins

[57] ABSTRACT

Apparatus and method for filtering the electrocardiograph (ECG) signal of a patient of unwanted signals, such as contamination signals produced by the use of nuclear magnetic resonance imaging system or muscle artifact signals. In a preferred embodiment, variable filter (2) is used to filter an input ECG signal (1). The filtering characteristics applied to the ECG signal by variable filter (2) vary in response to the logical state of a synchronization signal indicating a patient's biophysical state which is input to variable filter (2) via line (3). In alternative embodiments, a QRS detector (22), a delay circuit (20), and a pulse stretcher (21) may be used to provide a synchronization signal. In another alternative embodiment, a microprocessor (24) with an input ECG signal and with input data is used to control the filtering of the ECG signal in synchronization with a patient's ECG signal.

15 Claims, 6 Drawing Sheets

APPARATUS AND METHOD FOR FILTERING ELECTROCARDIOGRAPH SIGNALS

BACKGROUND OF THE INVENTION

This invention relates generally to an apparatus and method for filtering certain signals from electrocardiograph (ECG) signals, and more specifically, to an apparatus and method that automatically filters out unwanted signals from a patient's ECG signal.

Nuclear magnetic resonance imaging (sometimes referred to as magnetic resonance imaging and sometimes hereinafter referred to as "MRI") has been used increasingly in the last few years to replace and supplement the use of X-rays in computerized axial tomagraphy (CAT-scan) imaging because of the inherent danger to the human body presented by the use of X-rays in CAT-scan imaging. MRI, because it involves putting a patient within a magnetic field and obtaining cross sections of various selected internal portions of the human body without the X-rays used in CAT-scan imaging, eliminates many of the dangers inherent in CAT-scan imaging. MRI also is used to provide a more accurate image than provided by X-rays.

It is often desirable to use MRI equipment for sampling or collecting data while simultaneously monitoring the ECG signal of a patient. The use of MRI equipment for collecting data or sampling while the patent's ECG signal is monitored, however, often causes the ECG signal to be contaminated with unwanted signals. The contamination of the ECG signal caused by the concurrent use of MRI equipment for sampling or collecting data often results in an ECG signal which cannot effectively be used for confident monitoring of the patient. Because it is often desirable to monitor a patient's ECG signal while MRI equipment is used for sampling or collecting data, it is desirable to filter the unwanted electrical signals caused by the MRI equipment that contaminate the ECG signal.

In addition, greater clarity of the image produced by MRI is possible when the activation of an MRI system is synchronized with the patient's cardiovascular cycle. Because many of the body's tissues move when a heartbeat occurs, a blurred image may result from MRI if the imaging is done while a heartbeat occurs. Filtering the ECG signal of the contamination produced by an MRI system avoids the problem of having the MRI system trigger on false signals.

Although it is desirable to filter out the signals which contaminate an ECG signal, excessive filtering of the ECG signal must be avoided because of the risk that useful portions of the ECG signal might be inadvertently filtered and removed from the ECG signal. Consequently, it is desirable that the filtering of the ECG signal eliminate only the contamination signals caused by the use of MRI equipment or by other sources.

Filtering signals from various sources, such as muscle artifacts from muscle contractions and contamination signals from power supplies, from an ECG signal has been accomplished in the past through various means. The use of MRI systems, however, creates a different contamination signal than other contamination signals such as muscle artifacts or signals from power supplies. The frequencies of muscle artifact contamination signals and contamination signals from power supplies generally are more easily removed from an ECG signal than is a contamination signal from an MRI system. For example, immobilizing the patient and careful placement of the electrodes can eliminate much of the muscle artifact contamination signal. Signals from power supplies, on the other hand, are of a fairly precise frequency which does not vary greatly over a short time period. Consequently, it is usually easy to filter only at the specific frequencies of the power supply contamination signal and thereby avoid excessive filtering of the ECG signal.

MRI systems generally produce contamination signals over roughly the same range of frequencies as the signals of a patient's heart. Also, the MRI contamination signal varies among different MRI systems. Consequently, filtering an ECG signal to remove unwanted signals resulting from the use of MRI systems for sampling or collecting data presents a problem distinct from filtering an ECG signal of electrical signals from other sources.

SUMMARY OF THE INVENTION

The invention generally is designed to activate a filter with a first set of predetermined characteristics at a specific predetermined point in the QRS waveform of an ECG signal of a patient. The predetermined point in the QRS waveform is used to synchronize the activation of MRI equipment for sampling or collecting data. The first set of predetermined filtering characteristics is chosen to filter the unwanted signals caused by the use of MRI for sampling or collecting data. At a different predetermined point in the QRS waveform, however, when the MRI equipment is not in such use, the invention varies the filtering characteristics to a second set of predetermined characteristics in synchronization with the discontinuation of the use of the MRI equipment for sampling or collecting data. The second set of filtering characteristics is chosen to eliminate any unnecessary filtering of the ECG signal.

Upon the repetition of the first predetermined point in the QRS waveform, the invention again automatically varies the filtering characteristics to the first set of predetermined characteristics. During the successive repetitions of the patient's QRS waveform, the invention varies the filtering characteristics applied to the ECG signal in synchronization with the ECG signal. Since the MRI equipment is selectively activated for such use in synchronization with the ECG signal, the invention avoids filtering the ECG signal of the unwanted signals caused by such use of the MRI equipment when the MRI equipment is not actually in use for sampling or data collection. The invention, however, filters such signals from the ECG signal during the time when the MRI equipment is in such use. As noted in more detail below, a microprocessor is used in an alternative embodiment to provide a control system. In addition, the invention also effectively filters muscle artifact signals which occur within the general frequency range of the ECG signal of a patient. Although muscle artifacts usually occur over a range of frequencies, the invention, by varying the filtering characteristics applied to the ECG signal, can effectively filter most of the muscle artifact signal without excessively filtering the QRS waveform being monitored.

Accordingly, it is an object of the invention to provide an apparatus for filtering unwanted signals from an ECG signal of a patient in synchronization with the patient's QRS waveform.

It is also an object of the invention to provide an apparatus for filtering unwanted signals caused by the use of MRI equipment for sampling or collecting data from an ECG signal of a patient.

It is also an object of the invention to provide an apparatus for filtering unwanted muscle artifact signals from an ECG signal of a patient.

It is a further object of the invention to provide an apparatus for varying the filtering of an ECG signal by synchronizing the filtering means with the patient's QRS waveform.

It is still a further object of the invention to provide an apparatus for synchronizing the use of MRI equipment for sampling or collecting data with varying the filtering of the patient's QRS waveform.

It is still a further object of the invention to provide a control system with a microprocessor for filtering unwanted signals from an ECG signal of a patient in synchronization with a patient's QRS waveform.

It is still a further object of the invention to provide a method for filtering unwanted signals from an ECG signal in synchronization with the patient's QRS waveform.

The foregoing and other objects and advantages of the invention disclosed herein, which may generally be characterized as an apparatus and method for filtering ECG signals, will be apparent in the following description of the preferred embodiment and alternative embodiments of the invention.

DETAILED DESCRIPTION OF THE PREFERRED EMBODIMENT

In order to afford a more complete understanding of the invention and an appreciation of its advantages, descriptions of a preferred embodiment of the invention and of alternative embodiments of the invention are presented below.

Figure 1:
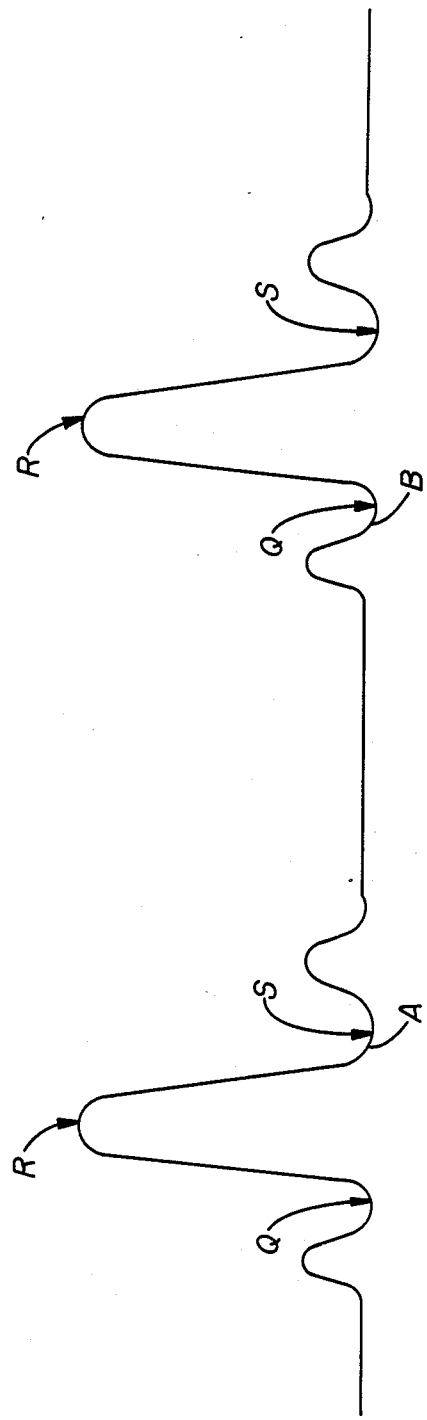
FIG. 1 illustrates a typical electrocardiographic (ECG) signal of a patient's QRS waveform.
Figure 2:
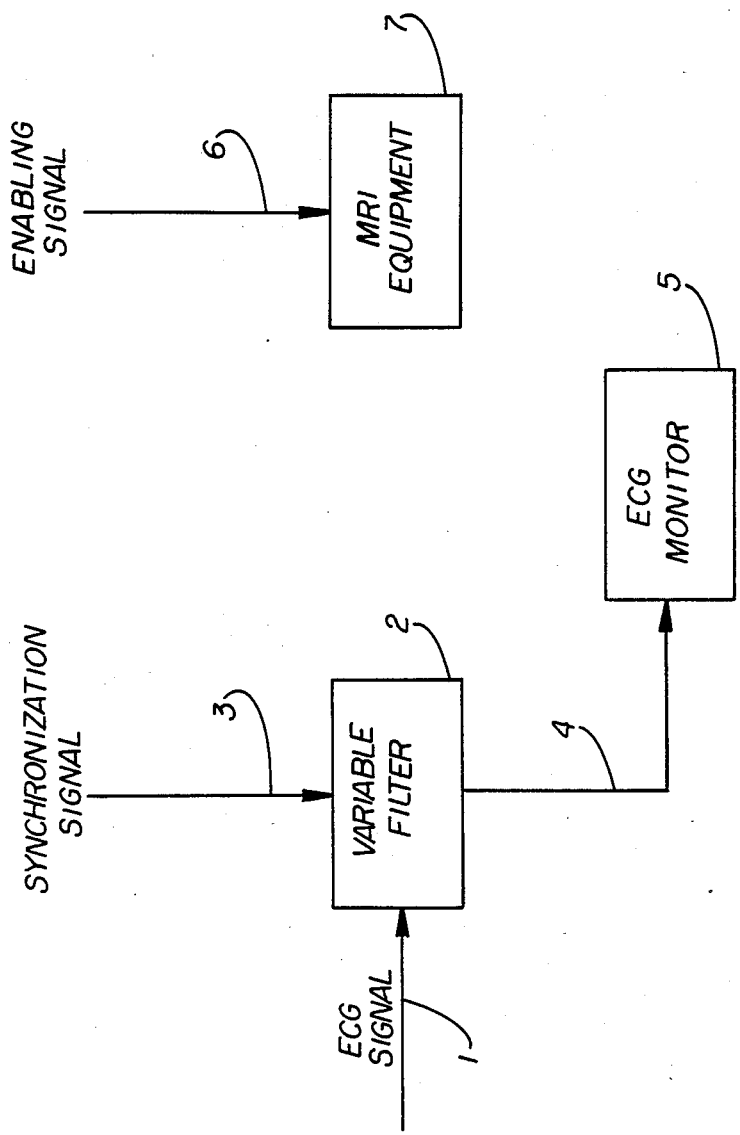
FIG. 2 illustrates a block diagram of a preferred embodiment of the present invention in which a variable filter is used to filter an input ECG signal in response to a synchronization signal.
Figure 4:
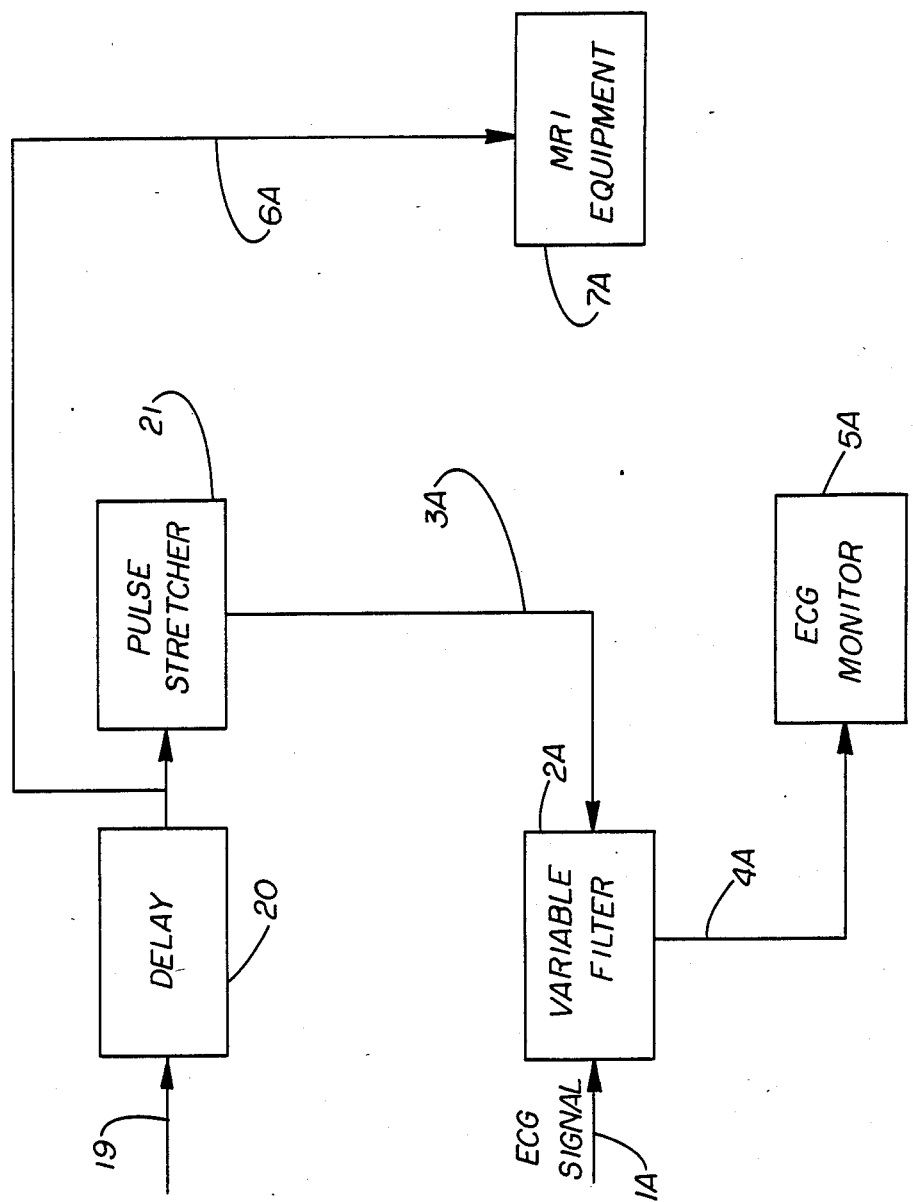
FIG. 4 illustrates a block diagram of an alternative embodiment of the present invention in which a delay circuit and a pulse stretcher are used to provide a synchronization signal.
Figure 5:
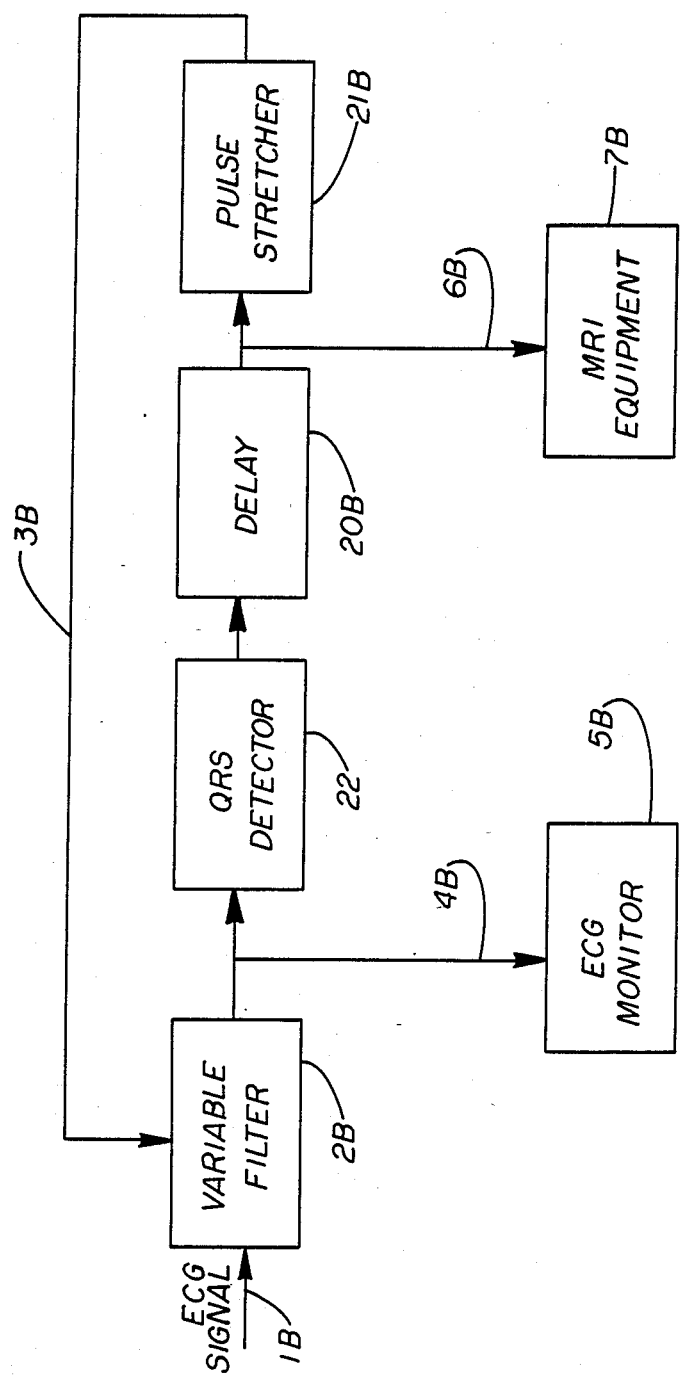
FIG. 5 illustrates a block diagram of a second alternative embodiment of the present invention in which a QRS detector is used to indicate a predetermined biophysical state of a patient.

Referring to FIG. 1, which is an illustration of a typical ECG signal waveform and which is utilized with the embodiments shown in FIG. 2, FIG. 4, and FIG. 5, the typical QRS waveform of a patient's heartbeat is shown. Two complete cycles of the QRS waveform are shown in FIG. 1. The Q, R, and S portions of a patient's QRS waveform are shown by FIG. 1.

It is often desirable to use MRI equipment for data acquisition during a specific period within the QRS waveform of the patient's cardiovascular cycle. "Use" of MRI equipment includes, without limitation, the utilization of MRI equipment for data acquisition, such as sampling, collecting data or imaging. Means for detecting the occurrence of a predetermined biophysical state of a patient being monitored through use of the patient's ECG signal are well known in the art. Typically, the occurrence of an R wave is the predetermined biophysical state detected because of the relatively larger size of the R wave and its stability. It is possible, however, to select other portions of a QRS waveform as a predetermined biophysical state. Means for using the occurrence of the R wave of an ECG signal as a trigger for generating a signal which serves as an enabling signal and which can be used to selectively activate additional biophysical equipment, such as MRI equipment, at some point in the QRS waveform, such as point A as shown in FIG. 1, are also well known in the art.

Once activated, it is often desirable to use the MRI equipment for sampling or data collection from the patient for a specific time period. The MRI equipment can be deactivated upon the generation of an electric signal after a predetermined period of time from the occurrence of a predetermined biophysical state of a patient such that the MRI equipment is deactivated and ceases to be so used at some predetermined point in the second repetition of the QRS waveform, such as point B as shown in FIG. 1.

FIG. 2 is a block diagram illustrating the components of an electrical circuit which is a preferred embodiment of the invention. Referring now to FIG. 2, an input electrocardiograph (ECG) signal of a patient appears on line 1 as an input to a variable filter 2. Unwanted signals, such as electrical signals produced by the use of MRI systems or muscle artifacts, often contaminate the ECG signal of a patient being monitored.

The variable filter 2 provides means for filtering unwanted signals, such as those caused by the use of MRI equipment or muscle artifacts, from the input ECG signal on line 1. Variable filter 2 acts as either a low pass filter with a 3dB point of approximately fifty (50) Hertz (i.e. a fifty (50) Hz low pass filter) or as a low pass filter with a 3dB point of approximately five (5) Hertz (i.e., a five (5) Hz low pass filter), depending upon the logic state of line 3, which is also an input into variable filter 2.

Line 3 provides means for transmitting a synchronization signal to variable filter 2 for selecting the predetermined filtering characteristics of variable filter 2. When the synchronization signal on line 3 is in a low logical state, variable filter 2 acts as a fifty (50) Hz low pass filter. Conversely, when line 3 is in a high logical state, variable filter 2 acts as a five (5) Hz low pass filter. In this preferred embodiment, the predetermined filtering characteristics of variable filter 2 are selected as a low pass filter with a 3dB point of approximately fifty (50) Hertz and a low pass filter with a 3dB point of approximately five (5) Hertz. The frequencies of the 3dB points of variable filter 2 may vary. For example, depending on the MRI equipment used and other factors, additional filters or different predetermined filtering characteristics may be chosen.

The synchronization signal which is transmitted by means of line 3 to variable filter 2 can be generated in a variety of ways as detailed in the descriptions of alternative embodiments of the invention below. The synchronization signal on line 3 is generated so that it contains a high logical signal during the time when the MRI equipment is in use for sampling or collecting data and variable filter 2 is to act as a five (5) Hz low pass filter. Conversely, a low logical signal is generated as the synchronization signal on line 3 when the MRI equipment is not in such use and variable filter 2 acts as a fifty (50) Hz low pass filter.

Figure 3:
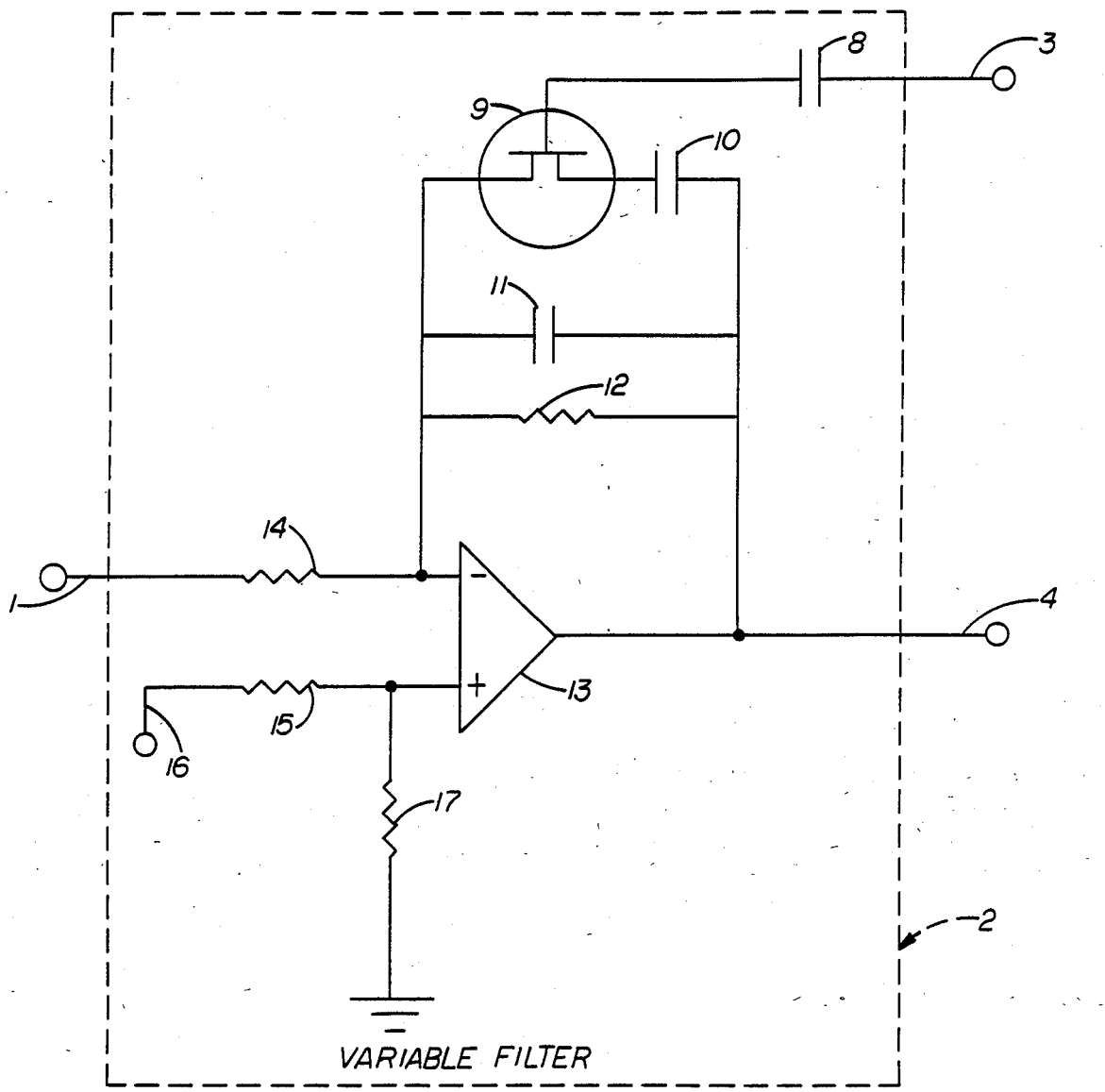
FIG. 3 illustrates a detailed schematic diagram of a variable filter utilized with the embodiment of FIG. 2.

Variable filter 2 is shown in detail in FIG. 3. Referring now to FIG. 3, the operation of variable filter 2 is as detailed below. The synchronization signal on line 3 is input to variable filter 2 and passes through a first capacitor 8, which is connected in series with the synchronization signal on line 3. Capacitor 8 in this preferred embodiment has a selected value of seventy-five (75) picofarads. It is noted that, in theory, capacitor 8 could be replaced by a resistor with a high resistance, such as one (1) megohms.

After passing through capacitor 8, the synchronization signal from line 3 is input into the gate of an n-channel enhancement mode Field Effect Transistor (FET) 9 of a type well known in the art. The source of FET 9 is connected in series to a second capacitor 10. Capacitor 10 in this preferred embodiment has a selected value of 0.20 microfarads.

Capacitor 10 and FET 9 are connected in parallel with a third capacitor 11 and a first resistor 12. Capacitor 11 and resistor 12 have selected values of 0.022 microfarads and one hundred fifty (150) kilo-ohms, respectively. Capacitor 10 and FET 9, capacitor 11, and resistor 12 are connected, in parallel, with the inverting input and the output of operational amplifier (op amp) 13.

Op amp 13 is commercially available and is well known in the art. In this preferred embodiment, op amp 13 is a quad self-compensated amplifier and is used as a 1 to 1 inverting amplifier. The output signal provided by op amp 13 is a filtered ECG signal of a patient and is transmitted by means of line 4.

Line 1 provides an input ECG signal, which passes through a second resistor 14. Resistor 14 is connected in series with the input ECG signal on line 1 and the signal which is input to the inverting input of op amp 13. Resistor 14 in this preferred embodiment has a chosen value of one hundred fifty (150) kilo-ohms.

The noninverting input of op amp 13 is connected to ground through a third resistor 17, which is connected in series with ground. Resistor 17 has a chosen value of eighteen (18) kilo-ohms.

The noninverting input of op amp 13 is also connected to a voltage source 16, which maintains a DC voltage of five volts (+5V). Voltage source 16 is connected in series with a fourth resistor 15 which, in turn, is connected with the noninverting input of op amp 13. Resistor 15 has a chosen value of eighteen (18) kilo-ohms.

When the synchronization signal on line 3 is in a high logical state, FET 9 conducts and current flows through capacitor 10. Capacitor 10, capacitor 11, and resistor 12 are thus connected in parallel and, together with resistor 14, produce the desired filtering characteristics of variable filter 2 when the synchronization signal is in a high logical state.

When the synchronization signal on line 3 is in a low logical state, FET 9 does not conduct and current does not flow through capacitor 10. Consequently, capacitor 11 and resistor 12 are connected in parallel and, together with resistor 14, produce the desired filtering characteristics of variable filter 2 when the synchronization signal is in a low logical state.

As is well known in the art, the actual resistance and capacitance of resistors and capacitors, respectively, often varies from the specified value of the components. Consequently, it is expected that such variations will and may occur, with the result that variable filter 2 may act as a low pass filter with a 3dB point of approximately either fifty (50) Hz or five (5) Hz, instead of exactly at either fifty (50) Hz and five (5) Hz, the predetermined filtering characteristics of variable filter 2 in this preferred embodiment. In addition, it is possible for one skilled in the art to vary the values of the components of variable filter 2 without substantially affecting the operation or performance of variable filter 2.

Variable filter 2 also provides means for providing an output signal. Line 4 provides means for transmitting the output signal of variable filter 2 wherein the signal on line 4 is used for monitoring a patient. "Monitoring" includes, without limitation, such uses as: displaying, recording, diagnosing, or evaluating a patient's biophysical condition. Commonly, such monitoring will be done with monitoring equipment such as an ECG monitor 5, as is well known in the art and is shown in FIG. 2. Thus, referring to FIG. 2, the ECG monitor 5 is able to receive a signal free of unwanted signals, such as the contamination caused by the use of the MRI equipment 7 or by muscle artifacts, from variable filter 2 through line 4, since variable filter 2 acts as a fifty (50) Hz low pass filter when the MRI equipment 7 is not in such use and line 3 is in a low logical state, while variable filter 2 acts as a five (5) Hz low pass filter and thereby removes the unwanted signals when line 3 contains a high logical signal.

Line 6, as shown in FIG. 2, can be used to provide means for transmitting an enabling signal to MRI equipment 7, wherein the enabling signal can be used to synchronize the activation and deactivation of MRI equipment 7 for use for sampling or collecting data with the variation of the filtering characteristics of variable filter 2.

Referring now to FIG. 4, in which another embodiment of the invention is set forth, the synchronization signal is generated by a combination of elements in addition to the same elements as those described above.

As shown in FIG. 4, an input signal 19 indicating a predetermined biophysical state of a patient is input into means for synchronizing an output pulse signal with input signal 19. The synchronization means are provided, in this alternative embodiment, by a 0–250 millisecond (ms) delay circuit 20, of a type which is well known to those skilled in the art. The delay circuit 20 is preset so that its output pulse signal coincides with a predetermined point of the QRS waveform, such as point A as shown in FIG. 1. The predetermined point A in the QRS waveform, as shown in FIG. 1, coincides with a predetermined time from the time that the R wave of the QRS waveform occurs. Delay circuit 20 is preset to coincide with this predetermined period of time so that it generates a high logical output pulse signal which coincides with point A of the QRS waveform shown in FIG. 1. During successive repetitions of the QRS waveform, delay circuit 20 generates successive output pulse signals which correspond to the predetermined point in each QRS waveform, such as point A as shown in FIG. 1.

The output pulse signal of delay circuit 20 can be transmitted by means of line 6A to MRI equipment 7A for selectively activating the MRI equipment 7A for use for sampling or collecting data, as shown in FIG. 4.

The output pulse signal of delay circuit 20 is input to means for varying the time between the output pulse signals generated by delay circuit 20 during successive repetitions of the patient's QRS waveform. The time varying means are provided, in this alternative embodiment, by a 0-2000 millisecond (ms) pulse stretcher circuit 21, of a type which is well known to those skilled in the art. The pulse stretcher 21 is preset to correspond with the period of time during which the use of an MRI system is desired for sampling or collecting data; i.e., the length of time during which the MRI equipment is in such use. In practice, pulse stretcher 21 is preset so that the high logical signal which is output by pulse stretcher 21 and transmitted on line 3A occurs for approximately 90% of the period of the QRS waveform. Presetting pulse stretcher 21 in this manner avoids potential problems resulting from an overlap of the output signal of pulse stretcher 21 with the occurrence of the next R wave.

The pulse stretcher 21 generates a high logical output signal which is input through means for transmitting the output signal of pulse stretcher 21 to variable filter 2A. The transmission means are provided by line 3A which is connected to variable filter 2A.

The remainder of the system illustrated in FIG. 4 is identical to that of the embodiment of FIGS. 1-3 with similar reference numerals indicating similar elements with the addition of the letter A.

Referring now to FIG. 5, which is an alternative embodiment of the invention including, in addition to the same elements as those described above, means for detecting the occurrence of a predetermined state of an ECG signal. Said detection means are provided, in this alternative embodiment of the invention, by QRS detector 22, of a type which is well known to those skilled in the art. By way of example, the QRS detector 22 may be a slew rate detector. The output of variable filter 2B is input to QRS detector 22, which monitors the amplitude of the output ECG signal of variable filter 2B. Alternatively, the input ECG signal on line 1B could be input to QRS detector 22. QRS detector 22 is preset so that it generates a high logical output signal when an R wave from the QRS waveform of the selected input ECG signal from either line 1B or from variable filter 2B occurs. The output signal from QRS detector 22 is then input into delay circuit 20B.

Similarly, the invention in the alternative embodiment shown in FIG. 5 might include means for transmitting the output signal of delay circuit 20B to MRI equipment 7B. Said transmission means are provided, in the alternative embodiment of the invention as shown in FIG. 5, by line 6B which connects the output of delay circuit 20B with MRI equipment 7B. Thus, when delay circuit 3B generates an output pulse, line 6B will contain a high logical signal and line 6B can be used as an input to MRI equipment 7B to selectively activate the use of MRI equipment 7B for sampling or collecting data.

The remainder of the system illustrated in FIG. 5 is identical to that of the embodiment of FIG. 4 with similar reference numerals indicating similar elements with the addition of the letter B.

Figure 6:
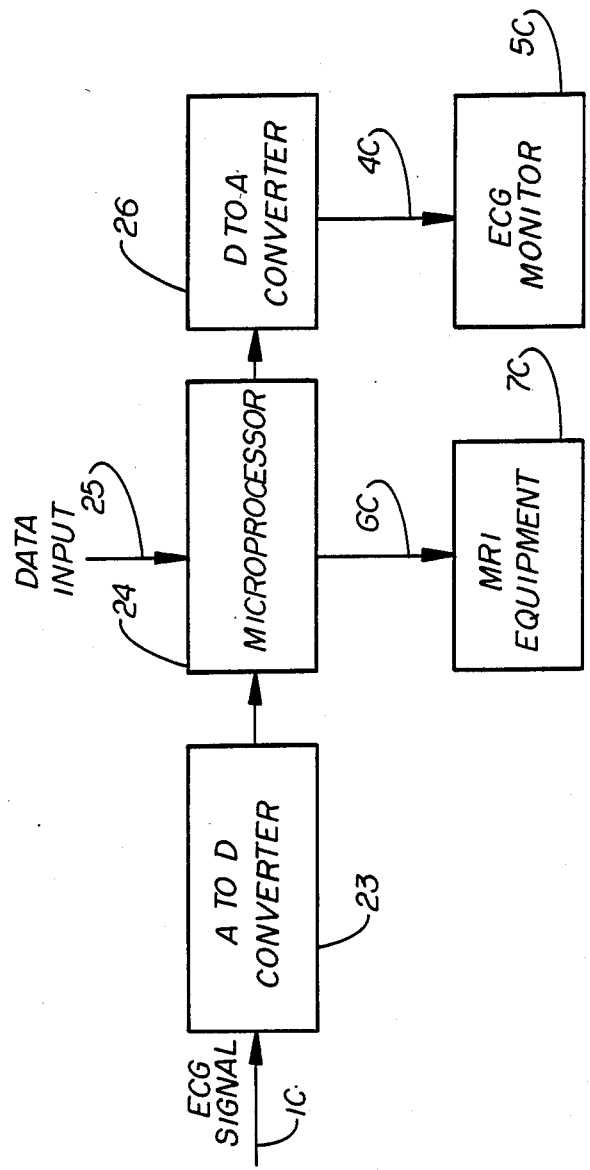
FIG. 6 illustrates a block diagram of a third alternative embodiment of the present invention in which a microprocessor is used for filtering an input ECG signal.

Referring now to FIG. 6, in which another alternative embodiment of the invention is illustrated, a microprocessor 24 is used to control the filtering of an input ECG signal. The input signal on line 1C is input to an analog to digital (A/D) converter 23. A/D converter 23 is of a type well known in the art and converts the input ECG signal from analog to digital form. The output of A/D converter 23 is input to microprocessor 24.

Microprocessor 24 is a microprocessor of a type well known in the art and is programmed to detect the occurrence of an R wave, or some other predetermined biophysical state of a patient being monitored, and to selectively activate MRI equipment 7C while simultaneously varying the filtering characteristics applied by microprocessor 24 to the digital ECG signal. Thus, microprocessor 24 simultaneously synchronizes the activation of MRI equipment 7C and the variation of the filtering characteristics applied to the ECG signal of the patient's QRS waveform. Microprocessor 24 thus is programmed to perform as a variable filter.

Microprocessor 24 is programmed to monitor the input ECG signal and, before the next occurrence of an R wave, or some other predetermined biophysical state of a patient, generates an output signal on line 6C which deactivates MRI equipment 7C. Microprocessor 24, in synchronization with the ECG signal, also varies the filtering characteristics applied by it to the ECG signal.

After filtering by microprocessor 24, the filtered ECG signal (still in digital form) is input to a digital to analog (D/A) converter 26. D/A converter 26 converts the digital ECG signal after filtering by microprocessor 24 to an analog form and provides the output signal via line 4C to ECG monitor 5C for monitoring.

Line 25 allows the input of data to microprocessor 24. Thus, a user can input, through line 25, information such as the length of time microprocessor 24 is to activate MRI equipment 7C, the predetermined filtering characteristics to be applied to the ECG signal by microprocessor 24, and other parameters of the operation of microprocessor 24 in regards to its functions.

It is also apparent that microprocessor 24 could be used in combination with other elements. For example, microprocessor 24 could be programmed to select among one of a number of different filters with predetermined filtering characteristics in synchronization with the QRS waveform of a patient, instead of being programmed to filter the ECG signal itself.

Additionally, other alternative embodiments of the invention may include variations of the embodiments described above. For example, as modifications and changes are made to experimental and commercial MRI equipment, slightly different contamination signals may be created in ECG signals from the operation of such modified MRI equipment. Thus, for example, the predetermined filtering characteristics of variable filter 2 or microprocessor 24 might be adapted to reflect such changes.

While only certain embodiments of the invention have been illustrated and described, it is apparent that alterations, changes, and modifications may be made without departing from the scope and spirit thereof.

What is claimed is:

1. An apparatus for filtering unwanted electrical signals from an electrocardiograph signal of a patient comprising:
   means for filtering an input electrocardiograph (ECG) signal of a patient and for providing an output signal therefrom;
   means for transmitting a synchronization signal indicating a biophysical state of said patient to said filtering means; and
   means responsive to said synchronization signal for varying said filtering means wherein said synchronization signal is used to select predetermined filtering characteristics, and wherein said filtering means comprises a plurality of low pass filters and wherein said plurality of low pass filters comprises one low pass filter with a 3dB point of approximately fifty (50) Hertz and one low pass filter with a 3dB point of approximately five (5) Hertz.

2. An apparatus for filtering unwanted signals from an electrocardiograph signal of a patient comprising:

a variable filter for filtering an input electrocardiograph (ECG) signal of a patient and for providing an output signal therefrom;

means for synchronizing an output pulse signal with an indicator signal indicating a predetermined biophysical state of a patient being monitored;

means connected to said output pulse signal for varying the time between output pulse signals of said synchronizing means and for providing an output signal therefrom;

means connecting said output signal of said time varying means for transmitting said output signal to said variable filter;

means responsive to said output signal of said time varying means for varying said variable filter wherein said output signal from said time varying means is used to select predetermined filtering characteristics of said variable filter; and means connected to said variable filter for transmitting said output signal of said variable filter means wherein said output signal is used for monitoring a patient.

3. An apparatus for filtering unwanted signals from an electrocardiograph signal of a patient comprising:

means for filtering an input electrocardiograph (ECG) signal of a patient, comprising a plurality of low pass filters having predetermined filtering characteristics, and for providing an output signal therefrom;

means for detecting a predetermined biophysical state of a patient being monitored from the patient's ECG signal and for providing an output signal therefrom;

means connected to said output signal of said detecting means for generating an output pulse signal and synchronizing said output pulse signal with said output signal of said detection means and for providing an output signal therefrom;

means connected to said output signal of said generating and synchronizing means for varying the time between output pulse signals of said generating said synchronizing means and for providing an output signal therefrom;

means connected to said output signal of said time varying means for transmitting said output signal of said time varying means to said filtering means;

means responsive to said output signal of said time varying means for varying said filtering means wherein said output signal of said time varying means is used to select predetermined filtering characteristics of said low pass filters of said filtering means; and means connected to said filtering means for transmitting said output signal of said filtering means wherein said output signal is used for monitoring a patient.

4. An apparatus for filtering unwanted electrical signals produced by nuclear magnetic resonance imaging (MRI) systems from an electrocardiograph signal of a patient comprising:

means for filtering unwanted electrical signals produced by MRI systems from an input electrocardiograph (ECG) signal of a patient and providing an output signal therefrom:

means for transmitting a synchronization signal indicating a biophysical state of said patient to said filtering means;

means responsive to said synchronization signal for varying said filtering means wherein said synchronization signal is used to select predetermined filtering characteristics; and means connected to said filtering means for transmitting said output signal of said filtering means wherein said output signal is used for monitoring a patient.

5. An apparatus for filtering unwanted electrical signals produced by nuclear magnetic resonance imaging (MRI) systems from an electrocardiograph signal of a patient comprising:

means for filtering unwanted electrical signals produced by MRI systems from an input electrocardiograph (ECG) signal of a patient and providing an output signal therefrom;

means for transmitting a synchronization signal indicating a biophysical state of said patient to said filtering means;

means responsive to said synchronization signal for varying said filtering means wherein said synchronization signal is used to select predetermined filtering characteristics and wherein said filtering means comprises a plurality of low pass filters and wherein said plurality of low pass filters comprises one low pass filter with a 3dB point of approximately fifty (50) Hertz and one low pass filter with a 3dB point of approximately five (5) Hertz; and means connected to said filtering means for transmitting said output signal of said filtering means wherein said output signal is used for monitoring a patient.

6. An apparatus for filtering unwanted electrical signals produced by nuclear magnetic resonance imaging (MRI) systems from an electrocardiograph signal of a patient comprising:

means for filtering unwanted electrical signals produced by MRI systems from an input electrocardiograph (ECG) signal of a patient and for providing an output signal therefrom;

means for synchronizing a pulse signal with an indicator signal indicating a predetermined biophysical state of a patient being monitored;

means connected to said pulse signal for varying the time between pulse signals of said synchronizing means and for providing an output signal therefrom;

means connecting said output signal of said time varying means for transmitting said output signal to said filtering means;

means responsive to said output signal of said time varying means for varying said filtering means wherein said output signal from said time varying means is used to select predetermined filtering characteristics; and means connected to said filtering means for transmitting said output signal of said filtering means wherein said output signal is used for monitoring a patient.

7. An apparatus for filtering unwanted muscle artifact signals from an electrocardiograph of a patient comprising:

means for filtering unwanted muscle artifact signals from an input electrocardiograph (ECG) signal of a patient and for providing an output signal therefrom;

means for generating an output pulse signal and synchronizing said output pulse signal with an indicator signal indicating a predetermined biophysical state of a patient being monitored;

means connected to said output pulse signal for varying the time between output pulse signals of said generating and synchronizing means and for providing an output signal therefrom;

means connecting said output signal of said time varying means for transmitting said output signal to said filtering means;

means responsive to said output signal of said time varying means for varying said filtering means wherein said output signal from said time varying means is used to select predetermined filtering characteristics; and means connected to said filtering means for transmitting said output signal of said filtering means wherein said output signal is used for monitoring a patient.

8. An apparatus according to either claim 6 or claim 7 further comprising:

means for detecting a predetermined biophysical state of a patient being monitored from the patient's ECG signal and for providing an output signal therefrom wherein said output signal of said detecting means is utilized by said synchronizing means.

9. In a system having electrocardiograph means for monitoring a patient's cardiovascular cycle and having nuclear magnetic resonance imaging means for data acquisition; the improvement which comprises:

means for filtering an input electrocardiograph (ECG) signal of a patient and providing an output signal therefrom;

means for transmitting a synchronization signal indicating a biophysical state of said patient to said filtering means;

means responsive to said synchronization signal for varying said filtering means wherein said synchronization signal is used to select predetermined filtering characteristics in synchronization with the activation of said nuclear magnetic resonance imaging means; and means connected to said filtering means for transmitting said output signal of said filtering means wherein said output signal is used for monitoring a patient.

10. In a system having electrocardiograph means for monitoring a patient's cardiovascular cycle and having nuclear magnetic resonance imaging means for data acquisition; the improvement which comprises:

means for filtering an input electrocardiograph (ECG) signal of a patient and providing an output signal therefrom;

means for transmitting a synchronization signal indicating a biophysical state of said patient to said filtering means;

means responsive to said synchronization signal for varying said filtering means wherein said synchronization signal is used to select predetermined filtering characteristics and to selectively activate said nuclear magnetic resonance imaging means; and means connected to said filtering means for transmitting said output signal of said filtering means wherein said output signal is used for monitoring a patient.

11. A control system for filtering unwanted signals from an electrocardiograph signal of patient comprising:

means for converting an input electrocardiograph (ECG) signal of a patient to digital form and providing an output signal therefrom;

means for filtering an input ECG signal of a patient and providing an output signal therefrom;

means for transmitting input data; and a microprocessor responsive to said output signal of said converting means and connected to said means for transmitting input data, said microprocessor providing control means for selectively activating nuclear magnetic resonance imaging systems and providing means for selecting predetermined filtering characteristics of said filtering means, wherein said predetermined filtering characteristics are synchronized by said microprocessor with a biophysical state of said patient.

12. A control system for filtering unwanted signals from an electrocardiograph signal of patient comprising:

means for converting an input electrocardiograph (ECG) signal of a patient to digital form and providing an output signal therefrom;

means for transmitting input data; and a microprocessor responsive to said output signal of said converting means and connected to said means for transmitting input data, said microprocessor providing control means for selectively activating nuclear magnetic resonance imaging systems, means for filtering said ECG signal of a patient, and means for selecting predetermined filtering characteristics of said filtering means, wherein said predetermined filtering characteristics are synchronized by said microprocessor with a biophysical state of said patient.

13. A method for filtering unwanted signals from an electrocardiograph signal of a patient comprising the steps of:

filtering an input electrocardiograph (ECG) signal of a patient and providing an output signal therefrom;

synchronizing a pulse signal with a signal indicating a predetermined state of said patient and providing an output signal therefrom;

varying the time between pulse signals as synchronized with a signal indicating a predetermined state of said patient and providing an output signal therefrom wherein means connected to said filtering means for transmitting said output signal of said filtering means wherein said output signal is used for monitoring a patient.

14. A method for filtering unwanted signals from an electrocardiograph signal of a patient comprising the steps of:

filtering an input electrocardiograph (ECG) signal of a patient and providing an output signal therefrom;

detecting the occurrence of a predetermined biophysical state of a patient being monitored and providing an output signal therefrom for synchronizing a pulse signal;

synchronizing a pulse signal with a signal indicating a predetermined state of a patient being monitored and providing an output signal therefrom;

varying the time between pulse signals as synchronized with a signal indicating a predetermined state of a patient being monitored and providing an output signal therefrom wherein said output signal provides said synchronization signal; and varying the filtering characteristics applied to said ECG signal in response to a synchronization signal wherein said synchronization signal is used to select predetermining filtering characteristics in synchronization with the ECG signal of a patient.

15. A method for filtering unwanted electrical signals produced by the use of nuclear magnetic resonance imaging (MRI) systems from an electrocardiograph signal of a patient comprising:

filtering unwanted electrical signals produced by MRI systems from an input electrocardiograph (ECG) signal of a patient and providing an output signal therefrom; and varying the filtering characteristics applied to said ECG signal in response to a synchronization signal indicating a biophysical state of said patient wherein said synchronization signal is used to select predetermined filtering characteristics in synchronization with the ECG signal of a patient.

* * * * *